United States Patent [19]

Foulke

[11] Patent Number: 4,747,164

[45] Date of Patent: May 31, 1988

[54] HAT AND METHOD FOR MAKING A HAT

[75] Inventor: Robert W. Foulke, Dana Point, Calif.

[73] Assignee: Packaging Industries Group, Inc., Hyannis, Mass.

[21] Appl. No.: 47,300

[22] Filed: May 8, 1987

[51] Int. Cl.⁴ .................................................. A42B 1/20
[52] U.S. Cl. .............................................. 2/171; 2/12; 2/175; 2/197; 2/200
[58] Field of Search .................... 2/171, 196, 175, 177, 2/195, 197, 200, 12

[56] References Cited

U.S. PATENT DOCUMENTS

| 2,988,743 | 6/1961 | Wagenfeld | 2/197 X |
| 4,246,659 | 1/1981 | Lyons | 2/175 |
| 4,335,471 | 6/1982 | Quigley | 2/12 |

FOREIGN PATENT DOCUMENTS

| 223966 | 2/1959 | Australia | 2/12 |
| 725339 | 1/1966 | Canada | 2/200 |
| 96454 | 6/1939 | Sweden | 2/12 |

Primary Examiner—Louis K. Rimrodt
Assistant Examiner—Judith L. Olds
Attorney, Agent, or Firm—Berman, Aisenberg & Platt

[57] ABSTRACT

A novelty pop-up hat includes a brim portion, an open crown portion and a plurality of slits in the edge of the brim portion, for conforming the hat to the shape of the head. Decorative shapes extend from the inner perimeter of the brim so that the decorations stand substantially vertically when the hat is worn. In a preferred embodiment, a hat is cut in an oval shape from a flat sheet of foamed plastic material, and a substantially circular opening is cut toward one end forming a headband at the back of the head and a visor to shade the face. The hat is made by a diecutting method from a single piece of foamed plastic or other material.

16 Claims, 2 Drawing Sheets

HAT AND METHOD FOR MAKING A HAT

FIELD OF THE INVENTION

The invention relates to a novelty hat and a method for making a novelty hat.

BACKGROUND OF THE INVENTION

Novelty items are often used for advertising, party favors, etc. Such items are generally inexpensive to manufacture and not long-lasting.

SUMMARY OF THE INVENTION

A pop-up hat of the invention is of one-piece construction, and includes a brim portion and an open crown portion surrounded by the brim portion. In a preferred embodiment, the hat has a substantially oval outer perimeter having a substantially circular, open crown portion scored toward one end for the user's head, defining a headband portion extending around the circular portion at the back of the head, and a visor portion extending around the circular portion at the front of the head. A plurality of slits are cut in the edge of the circular portion, the slits extending substantially perpendicularly outward to provide a flexible portion for adapting the hat to the shape of the head.

Decorative portions extend within the circular portion, attached to the inner perimeter of the circular portion. When a user wears the hat, the decorative portions pop-up and extend upwardly to provide an amusing and/or attractive appearance. The hat is die-cut from a single sheet of stock material, preferably foamed plastic material.

It is an object of the invention to provide a pop-up hat which is easy to wear and economical to manufacture.

It is another object of the invention to provide a decorative novelty hat.

It is yet another object of the invention to provide a method for making a decorative novelty hat from a sheet of stock material.

DETAILED DESCRIPTION OF THE INVENTION

Figure 1:
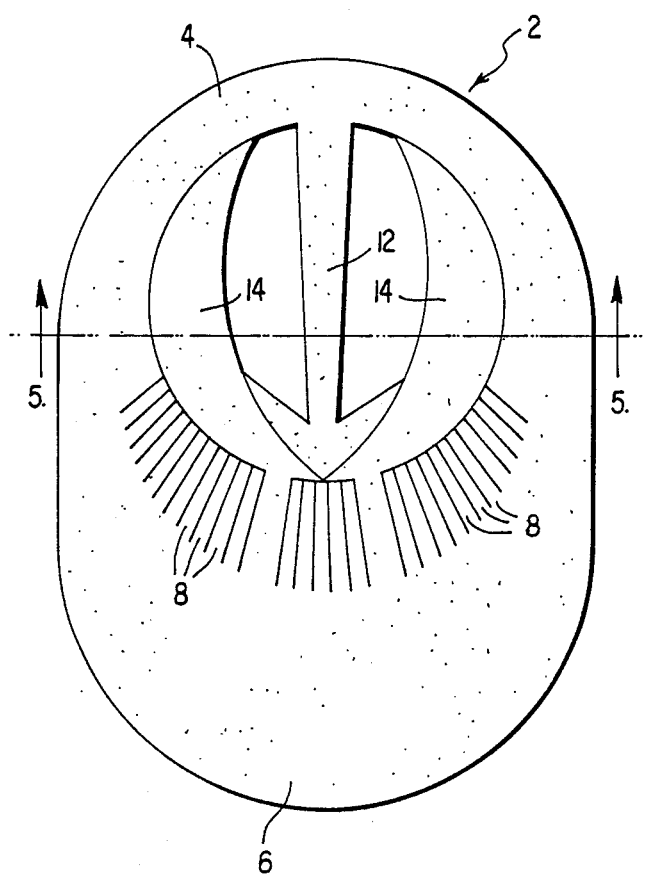
FIG. 1 is a top plan view of a hat of the invention.

The invention is a novelty pop-up hat or visor fabricated from a single sheet of stock material, preferably foamed plastic. Decorative portions are integrally formed during the one-step die-cutting method for producing the hat. When the hat or visor is worn by a user the decorative portions pop up and make an attractive or amusing novelty item which is long-lasting and may be re-used. The decorative portions, which stand up in use, may also be used for advertising purposes, incorporating initials, names, logos, etc. Decorative symbols such as lightning bolts, flowers, birds, etc. may be used. The hat is simple and economical to manufacture, since cuts and slits are scored in the plastic material enabling the hat to fit a full range of head sizes.

With reference to the figures, in which like numerals represent like parts, FIGS. 1 to 6 show examples of non-limiting embodiments of the invention. Hat 2, shown in FIG. 1, has a substantially oval outer perimeter 3 and a substantially circular opening 5 cut therein toward one end of hat 2 forming headband 4 around the back portion of the perimeter of the hat. The position of the substantially circular opening 5 at one end of the oval shape forms a headband portion 4 positioned at the back of the user's head and a visor portion 6 which shades the user's face.

Hat 2 is made from a single sheet of stock material, preferably foamed plastic. In order to provide a snug fit for a full range of head sizes, a plurality of slits 8 of about ½ to 2 in. long are scored into the visor portion adjacent the head. Slits 8 are cut through the foam sheet and extend substantially perpendicularly from the inner perimeter of the head portion outwardly toward the visor portion. The strip-like edge portions 9 between the slits separate at the head-adjacent edge when the hat is worn by a user, the degree of separation depending on the size of head. Slits 8 may also be cut in the back headband portion if required.

Decorative features may be cut from the material within the substantially circular portion 5. FIG. 1 shows an example of an appropriate decoration for a novelty hat which is suggestive of a "devil". The hat may, for example, be made of red foamed plastic. In the hat of FIG. 1, the decoration takes the form of an arrow-shaped devil's fork 12 and two crescent-shaped devil's horns 14. The decorations are shaped to fit within the perimeter of circular portion 5, enabling the entire hat to be die-cut in one operation. Decoration 12 extends upwardly from the back portion of headband 4 and decorations 14 extend upwardly from one or more front edge portions 9 when the hat is worn by a user, lower ends of decorations 12 and 14 each being adjacent the head when the hat is worn. Decorative portions 12 and 14, may extend from one or more edge portions 9. Edge portions 9 may be of different sizes, and larger portions 9 may be used to support decorative portions if necessary. Decorations may cover as much of the area of circular portion 5 as desired. Portions cut away from circle 5 are "waste" and may be used for another purpose or recycled.

Figure 2:
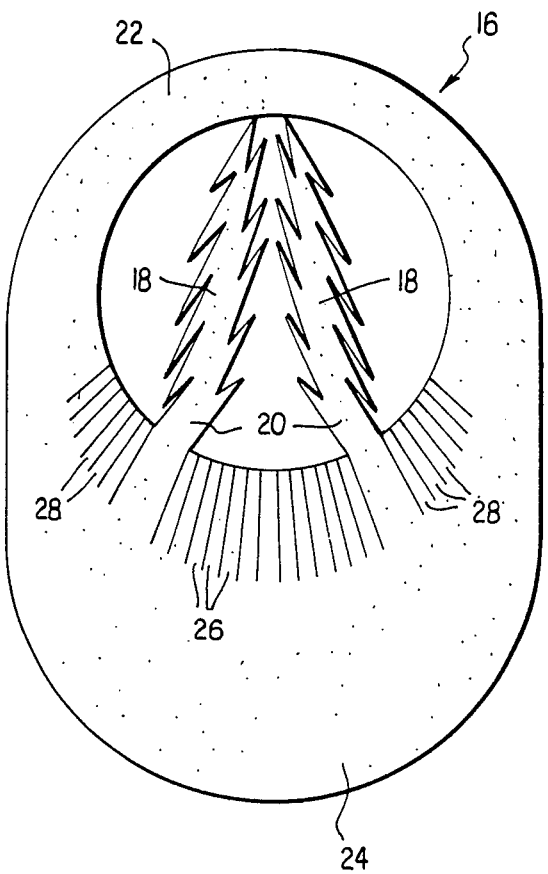
FIG. 2 is a top plan view of another hat of the invention.

FIG. 2 shows another hat 16, of the invention, in which the decorative portions take the form of lightning bolts 18. The base of each lightning bolt 18 is supported by edge portion 20. In use, headband portion 22 is placed at the back of the head, visor portion 24 shades the eyes, slits 26 separate edge portions 28 to form a comfortable edge for the visor portion at the edge of the hair, and lightning bolts 18 stand upright as decorative features.

Figure 3:
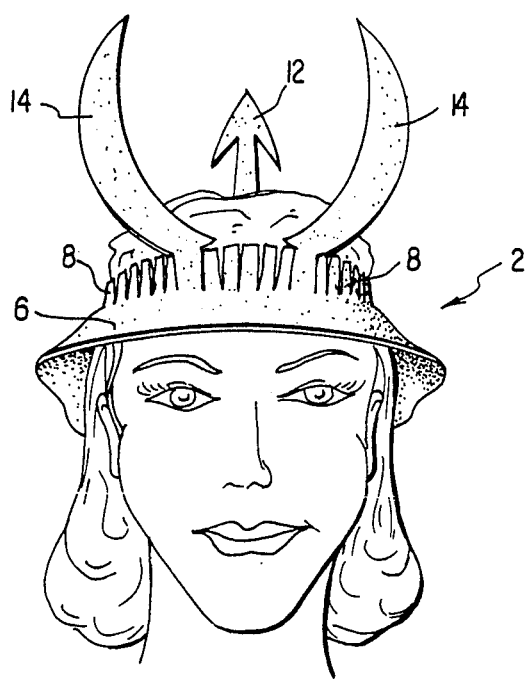
FIG. 3 is a front elevation view of a hat of FIG. 1 worn by a user.
Figure 4:
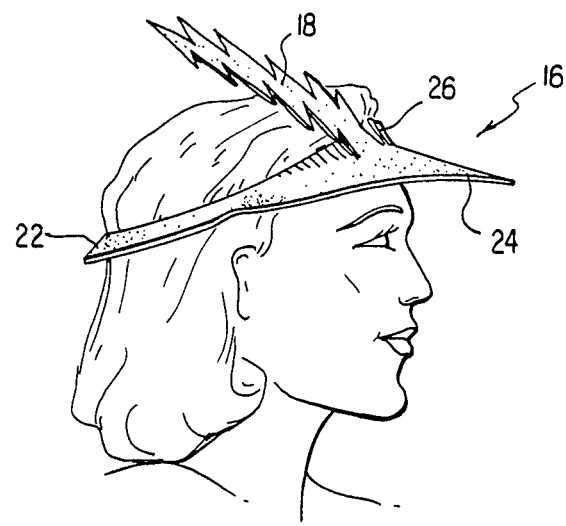
FIG. 4 is a side elevation view of a hat in FIG. 2 worn by a user.
Figure 5:
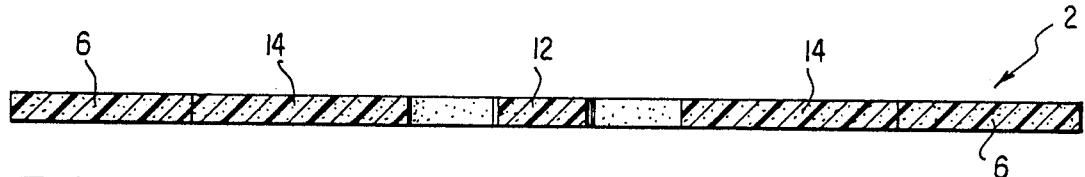
FIG. 5 is a cross-sectional view taken on line 5—5 of FIG. 1.

FIG. 3 shows a front view of the hat of FIG. 1 in use, and FIG. 4 shows a side view of the hat of FIG. 2, in use. It is clearly seen that the decorative portions are upstanding. FIG. 5 shows a cross-sectional view of the hat of FIG. 1 showing utilization of the material of circular opening 5 to form visor portions 6 and decorative portions 12 and 14.

If the outer perimeter of the hat is substantially circular instead of oval in shape, the opening for the head may be centrally positioned to provide a pop-up hat having the effect of a brim around an open-crown hat.

Figure 6:
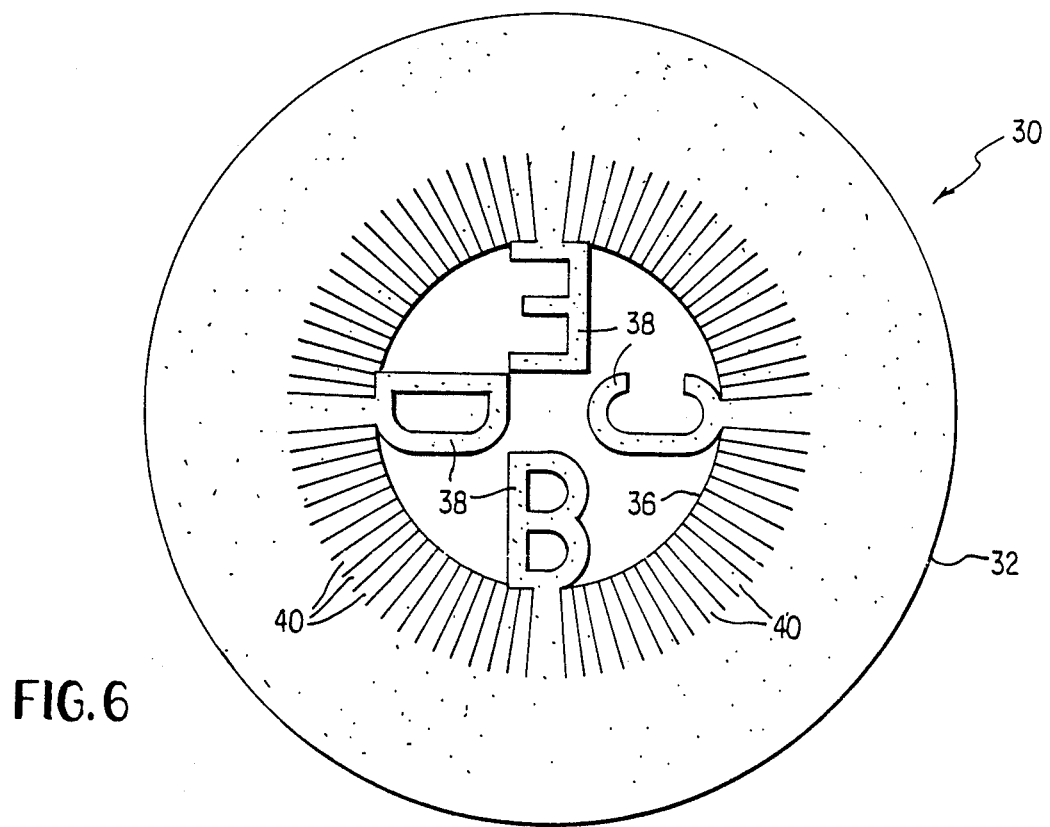
FIG. 6 is a top plan view of another hat of the invention.

The hat may also be scored with slits all around the head portion. Decorative portions are included as described. FIG. 6 shows a hat 30 of the invention cut in a circular shape 32 and having brim 34 surrounding open crown portion 36. Decorative portion 38 is in the form of a logo, and stands vertically when the hat is worn by a user, supported by edge portions 40. A hat of the invention may have any shape of outer perimeter, for example, a diamond shaped hat may be formed, or the edge may be scalloped or cut into other decorative shapes.

When a user wears a hat of the invention, the decorative portions pop up, and the material of the hat should be sufficiently flexible for the hat to be comfortable when the slit portions separate to conform to the shape of head. The material should also be sufficiently stiff that the decorative portions stand upright. Foamed plastic is suitable for making the hat. Unfoamed plastic may also be used, or a laminate of different plastic materials, either foamed or unfoamed may be used. Hats of the invention may provide a means for using up ends of rolls or off-cuts, thus avoiding waste.

Preferred material is foamed plastic between about ⅛ in. and ¼ in. in thickness. Thickness below about ⅛ in. makes the hat insufficiently rigid, and if the foam is more than about ¼ in. in thickness, the hat may be too stiff for comfort. A preferred thickness of foamed material is about 3/16 in., and a preferred material is closed cell polyethylene foam. A suitable density of foamed polyethylene used for making a hat of the invention is about 3 to 5 lb./cu. ft., a density of about 4 lb./cu. ft. being preferred. Open cell polyurethane foam having a density of about 2 to 7 lb./cu. ft. may also be used. Cross-linked foams are suitable. Other materials are known to one skilled in the art, for example, plastic sheet material (unfoamed), fabrics, flexible laminates, etc. may be used.

In a non-limiting example, a typical hat of FIG. 1 has a length from back to front of about 13 in. a width from side to side of about 9 in. and circular opening 5 has an inner diameter of about 6 in. Headband 4 has a width of about 1 in. at the back of hat 2, slits 8 extend about ½ in. to 2 in. in length toward the visor portion, and the unperforated section of visor portion 6 extends forward about 4 in. from the base of slits 8 forming the front of hat 2.

The hats of the invention are preferably made by diecutting, using a steel rule die, which has a sharp steel edge configured according to the outline to be cut. A roll of stock material to be used for the hats, for example, foamed plastic sheet material, is unrolled and placed on a hard surface, and the hat shapes are die cut through one or more layers of stock material, in a single cutting step, using methods known to one skilled in the art. A die may be made for one or more hats, enabling substantial savings of time if a plurality of hats are die cut in a single stamping operation.

If a two-color laminate is used, the hat and decorations will be of different colors on each side, creating a further novel effect.

While the invention has been described above with respect to certain embodiments thereof, it will be appreciated that variations and modifications may be made without departing from the spirit and scope of the invention.

What is claimed is:

1. A hat comprising:
   a brim portion defining an outer perimeter of the hat,
   an open crown portion defining an inner perimeter of the brim portion, and
   a plurality of head-conforming adjacent slits in a head-adjacent edge of the brim portion extending toward the outer perimeter of the hat,
   wherein at least one portion between said head-conforming adjacent slits extends from the head-adjacent edge of the brim portion forming a decorative portion which stands up when the hat is worn by a user.

2. A hat of claim 1 wherein the stock material comprises plastic material.

3. A hat of claim 2 wherein the plastic material comprises foamed plastic material.

4. A hat of claim 1 wherein the plurality of slits extend substantially perpendicularly to the head-adjacent edge of the brim portion.

5. A hat of claim 4 wherein the slits are about ½ to 2 in. in length.

6. A hat of claim 3 wherein the foamed plastic material comprises foamed polyethylene.

7. A hat of claim 6 wherein the foamed polyethylene has a density of about 3 to 5 lb./cu. ft.

8. A hat of claim 3 wherein the foamed plastic material comprises foamed polyurethane.

9. A hat of claim 8 wherein the foamed polyurethane has a density of about 2 to 7 lb./cu. ft.

10. A hat of claim 3 wherein the foamed plastic material is about ¼ in. to ⅛ in. in thickness.

11. A hat of claim 3 wherein the foamed plastic material comprises closed cell polyethylene foam, having a density of about 4 lb./cu. ft. and a thickness of about 3/16 in.

12. A hat of claim 1 wherein the entire hat is cut in one piece from a single sheet of stock material.

13. A hat of claim 1 wherein the plurality of adjacent slits are located in the front brim portion of the hat.

14. A hat of claim 13 further comprising at least one decorative portion spaced away from the plurality of adjacent slits, extending upwardly from the back brim portion when the hat is worn by a user.

15. A hat of claim 14 wherein the entire hat is cut in one piece from a single sheet of stock material.

16. A hat comprising a substantially oval shape cut from a sheet of foamed plastic material, said hat further comprising a substantially circular opening cut therefrom for accommodating the head of a user, said opening positioned toward one end of said oval shape at a distance therefrom forming a headband at said one end and a visor at the other end of said oval shape, and a plurality of adjacent slits extending substantially perpendicularly from the edge of said circular opening adjacent said visor toward said visor a sufficient distance to provide head-conforming flexibility to the hat for accommodating said user's head, and at least one decorative portion extending within said circular opening from a portion between adjacent slits, and attached to the inner edge of the circular opening, said at least one decorative portion standing up when the hat is worn by a user.

* * * * *